United States Patent [19]
Javdani et al.

[11] Patent Number: 5,852,215
[45] Date of Patent: Dec. 22, 1998

[54] PROCESS FOR THE PRODUCTION OF AZOMETHINES AND ALPHA-HALOACETANILIDES

[75] Inventors: Kambiz Javdani; Louie A. Nady, both of Daphne, Ala.; Ping H. Sih, Bend, Oreg.; Gilbert Rodriguez, Semmes, Ala.

[73] Assignee: Zeneca Limited, London, England

[21] Appl. No.: 719,298

[22] Filed: Sep. 19, 1996

Related U.S. Application Data

[60] Provisional application No. 60/004,181, Sep. 22, 1995.
[51] Int. Cl.$^6$ .................................................. C07C 249/02
[52] U.S. Cl. ........................ 564/277; 564/211; 564/214; 564/271; 564/276; 564/300
[58] Field of Search ..................................... 564/211, 214, 564/271, 276, 277, 300

[56] References Cited

U.S. PATENT DOCUMENTS

| | | | |
|---|---|---|---|
| 3,637,847 | 1/1972 | Olin | 260/562 B |
| 4,399,306 | 8/1983 | Domjan et al. | 564/214 |
| 4,491,672 | 1/1985 | Richarz et al. | 564/271 |
| 5,155,272 | 10/1992 | Baldus et al. | 564/214 |
| 5,298,659 | 3/1994 | Langer et al. | 564/271 |
| 5,399,759 | 3/1995 | Rodriguez | 264/214 |

*Primary Examiner*—Peter O'Sullivan
*Attorney, Agent, or Firm*—Joel G. Ackerman

[57] ABSTRACT

Aromatic azomethines are produced by continuous reaction of an aniline with a formaldehyde source, with continuous evaporation to remove residual water of reaction. The azomethine product may be further reacted, either continuously or in batch process, with a haloacetylating agent, and, additionally, with an aliphatic alcohol.

10 Claims, No Drawings

PROCESS FOR THE PRODUCTION OF AZOMETHINES AND ALPHA-HALOACETANILIDES

BACKGROUND AND PRIOR ART

This invention relates to the production of azomethines by the reaction of aniline with a source of formaldehyde (as described hereinbelow) and also to an improved process for production of haloacetanilides from anilines by reaction of the latter with a formaldehyde source to form azomethine, reaction of the azomethine with an acyl halide and, if an N,N-disubstituted haloacetanilide is the ultimate product, further reaction with an appropriate agent, for example, an alcohol.

In general, processes for the production of haloacetanilides in this manner are described in U.S. Pat. Nos. 3,630,716; 3,637,847; 4,097,262 and 5,399,759.

The latter patent, in particular, describes a process for production of azomethines and ultimately alpha-haloacetanilides by reaction of the aniline with a source of formaldehyde (termed in the patent a "formaldehyde-alcohol complex" produced by contacting paraformaldehyde with from about 0.25 to about 3 mole equivalents of an aliphatic alcohol having from 1 to 4 carbon atoms in the presence of a catalytic amount of a base. The process as described in that patent is a batch process and the several steps ultimately leading to the production of the alpha-haloacetanilide can be carried out either in separate reactors or reaction apparatus, or even in a "one-pot" operation, i.e., all steps are carried out in a single reactor.

The process described in U.S. Pat. No. 5,399,759 provides a number of advantages over the prior art such as quicker reaction between the formaldehyde source and the aniline, enablement of the use of paraformaldehyde as a feed to the process without the previously-encountered problems of paraformaldehyde sublimation and deposition on equipment, etc. However, there is still room for improvement.

For example, improvement could be made in the method of removing water of reaction. As disclosed in the patent, the water is removed from the reaction products by azeotropic distillation. Preferably the distillation is conducted continually during most of the course of the reaction, commencing shortly after the reaction itself starts. However, complete removal of the water of reaction is desired in order to drive the reaction to completion, and distillation in this fashion takes quite some time to remove all the water, if in fact complete removal even occurs.

Additionally, there will be a desire to minimize the reaction or residence time of materials in the azomethine production step, because undesirably long residence times could result in product degradation.

SUMMARY OF THE INVENTION

This invention comprises:

In a process for the production of an aromatic azomethine by reaction of an aniline with a source of formaldehyde, in which the formaldehyde is provided in the form of a product produced by contacting paraformaldehyde with from about 0.25 to about 3 mole equivalents of an aliphatic alcohol having from 1 to 4 carbon atoms in the presence of a catalytic amount of a base, the steps comprising: (a) conducting the reaction continuously; and (b) continuously evaporating water of reaction from the reaction mixture.

DETAILED DESCRIPTION OF THE INVENTION

The overall process, including both the production of azomethine and the ultimate production of alpha-haloacetanilides is described in U.S. Pat. No. 5,399,759, the disclosure of which is incorporated herein by reference. In general, that patent describes a batch process for the production of azomethines and ultimately alpha-haloacetanilides. In the azomethine step, a reactive form of formaldehyde, supplied as described below, is reacted with an aniline to produce an azomethine.

The aniline in general has the formula

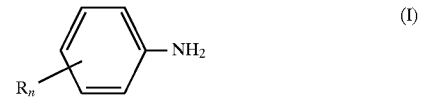

in which R represents hydrogen or one or more substituents which are relatively non-reactive with formaldehyde, particularly alkyl, alkoxy, or halogen; n is generally at a value of from 0 to 5, and is preferably 0, 1, 2 or 3. Herbicidal anilides or haloacetanilides are often prepared from anilines having one or more such substituents in the ortho position(s). Some typical starting anilines for this process, when used to ultimately prepare herbicidal anilides or haloacetanilides, include 2,6-dimethylaniline, 2,6-diethylaniline, 2-methyl,6-ethylaniline, 2-methyl,6-tertiary-butylaniline, 2-tertiary-butyl,6-haloanilines, 2,4-dimethylaniline, 2-tertiary-butyl-5,6-dimethylaniline, 2,6-dimethyl-3,4,5-trichloroaniline, 2-methylaniline, 2-ethylaniline, 2-methoxyaniline, and 2-ethoxyaniline.

The reaction products are primarily an azomethine and water, together with various by-products or impurities.

The formaldehyde source is provided in the form of a product of the contacting of solid paraformaldehyde with from about 0.25 to about 3 mole equivalents of an aliphatic alcohol having from 1 to 4 carbon atoms in the presence of a catalytic amount of a base. The contacting step may either be carried out in a separate piece of apparatus or may be carried out in the main reactor for the azomethine production, and in general is carried out at a temperature of about 85°–95° C. An inert solvent, for example an aromatic solvent such as xylene, may be present, but is not required.

The base utilized may be an organic or inorganic base such as an alkali metal hydroxide, alkoxide, carbonate or oxide, or a tertiary amine, with tertiary amines preferred. Typical catalysts for this technique include sodium hydroxide, potassium hydroxide, sodium methoxide, trialkylamines such as trimethylamine, triethylamine, and tri-n-butylamine, and heterocyclic amines including pyridine, N-alkylpiperidines and -pyrrolidines (for example, N-ethylpiperidine and N-methylpyrrolidines), tetra-alkylguanidines and fused bicyclic amines such as 1,8-diazabicyclo(5.4.0)undec-7-ene and 1,5-diazabicyclo(4.3.0)non-5-ene. The basic catalyst is generally used in an amount of from about 0.01 to about 1, preferably from 0.01 to about 0.05 mole equivalent, based on formaldehyde.

The azomethine production step may be carried out in the presence of a hydrocarbon solvent which forms an azeotrope with water at the reflux temperature of the solvent. Typical solvents include aromatic solvents such as benzene, toluene and xylene, and aliphatic and cycloaliphatic solvents such as n-hexane, n-heptane and cyclohexane. Depending on the solvent, the reflux temperature of the reaction mixture will range from about 80° C. to about 140° C. Preferably the reaction temperature is between 80° C. and about 100° C.

Alternatively, in the conduct of this invention, the reaction may be carried out without the use of a solvent.

In the case in which the process to produce azomethines is the first step in a multi-step process to produce herbicidal haloacetanilides, the final product (typically termed an α-haloacetanilide, or more commonly an α-chloroacetanilide) has the general formula

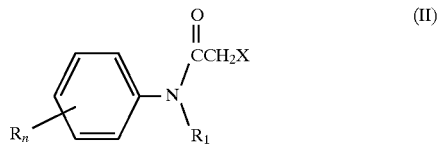 (II)

in which R and n are as described above; X is a halogen, usually chloro or bromo and most usually chloro, and $R_1$ is any of a number of substituents which have been described as components of herbicidal compounds, the most common of which tend to be various alkyl and alkoxyalkyl groups. Other substituents are described, for instance, in U.S. Pat. No. 4,097,262.

Of course, water is a product of the azomethine producing reaction, and its removal is necessary to drive the reaction to completion. Previously, the water has been removed by distillation, either during the reaction or subsequent to its apparent completion. However, the conduct of the azomethine production reaction in a batch process, together with the means so far utilized for removing water, have not proven entirely satisfactory. The reaction or residence time may be unduly lengthy, thus introducing the risk of possible product degradation. Additionally, it has proven difficult to remove residual amounts of water from the reaction mixture.

According to the present invention, the azomethine production step is run continuously rather than in a batch process, and the water of reaction is removed by continuous evaporation, as will be described in greater detail below.

The following are general descriptions of a number of embodiments of this invention.

In a first embodiment, the azomethine reaction mixture, containing the aniline and the formaldehyde-alcohol complex (optionally in the presence of a solvent) are mixed and heated and fed into one or a series of several downflow flooded evaporators. The operating temperature of the system is generally about 75°–105° and the pressure about 150–300 mmHg. The feed mixture is introduced from the top of the evaporators so that a countercurrent contact with the vapors is established. The azomethine product is collected from the bottom of the final evaporator in the series, and the distillate is recycled in order to prepare fresh quantities of formaldehyde-alcohol complex.

In a second embodiment, the azomethine production step is carried out in a series of two or more continuous upflow evaporators, with the temperature being about 75°–115° C. and pressure about 300–760 mmHg. In this embodiment, the reaction mixture is fed to the bottom of the evaporators so that a co-current flow of liquid and vapor is established in each evaporator. The liquid from the top of the final evaporator in this series is then fed to a falling film or downflow flooded evaporator to remove the residual water and drive the reaction to completion.

In a third embodiment, the azomethine production may be carried out in either downflow flooded evaporators or continuous upflow evaporators. The residual water is removed from the reaction mixture in one or more evaporators, each consisting of two sections—an upper section, which is a falling film section, and a lower section which is flooded. In this embodiment, most of the vapor is removed in the falling film section of each evaporator. The flooded section on the bottom of each evaporator provides additional residence time for completing the reaction. With most of the vapor having been removed in the top section, the amount of vapor released in the lower, flooded section will be small enough to keep the evaporator in a hydrodynamically stable condition.

In a fourth embodiment, the azomethine production step is carried out in one or more continuous stirred tank reactors, with the reaction product being then passed through one or more falling film evaporators operated at 95°–139° C. temperature and 200–760 mmHg pressure, and/or one or more flooded downflow evaporators operated at 75°–105° C temperature and 150–300 mmHg pressure.

In any of the above-described embodiments, the evaporator or evaporators may be a packed column. The use of such an evaporator can result in a slightly higher residence time for the reaction mixture and a higher vapor-liquid contact. When the packed column is a downflow evaporator, the packing increases the hydrodynamic stability of the evaporator and improves the heat and mass transfer efficiencies. Though in most cases a higher residence time would not be desirable as it could lead to product degradation, it can be tolerated to a certain extent in order to obtain better heat and/or mass transfer efficiency.

The evaporators used to remove residual water from the azomethine production step most preferably involve countercurrent contact of liquid and vapors.

Additionally, any of the evaporators in the embodiments described above may also include provision for sparging an inert gas such as nitrogen or an inert condensible vapor such as xylene, into the bottom of the evaporator. If xylene is used as the sparging vapor, it may be obtained by recovery and recycling of xylene solvent downstream in the process.

In further embodiments of this invention, the azomethine product, after removal of the water described above, is converted in two additional steps to an alphahaloacetanilide, with one or both additional steps being carried out continuously.

In the second step, the azomethine is reacted with a haloacetylating agent, usually chloroacetyl chloride, in an appropriate solvent. This produces a 2- or alpha-halo (preferably chloro) N-halomethyl (preferably chloromethyl) acetanilide which has the formula

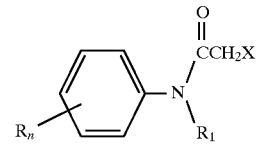

in which X is halo (usually chloro or bromo) and $R_1$ is halomethyl (chloromethyl or bromomethyl). Haloacetanilides of this type are described as herbicides in U.S. Pat. Nos. 3,630,716 and 3,637,847.

This step may be carried out continuously by feeding the azomethine and haloacetylating agent continuously into a single, or a series of, continuously-stirred tank reactors. These will be operated at temperatures ranging from ambient to about 80° C. under atmospheric pressure. Alternatively, the azomethine and haloacetylating agent are fed continuously into either a plug flow reactor or a pump reactor.

In the final step, the N-halomethyl product is reacted with an appropriate aliphatic alcohol to produce an N-alkoxyalkyl-alpha-haloacetanilide having the formula II described above. This step is again carried out continuously, for example, in one or a series of continuous tank reactors operated at temperatures from ambient to about 80° C. under atmospheric pressure. The product from the final reactor in this series is contacted with a base such as ammonia, triethylamine, or tri-(n-butyl)amine, and then transferred to a storage tank or further continuous stirred tank reactor to allow more residence time and drive the reaction to completion.

It should be noted that, for the practice of this invention, it is not required that all three stages in the production of alpha-haloacetanilides be carried out continuously. That is only the most preferred embodiment. It may be satisfactory if only the first stage, that is, the azomethine production step, is carried out continuously and the second and third stages carried out as batch processes, as in the prior art. Alternatively, the first and second stages of this process may be carried out continuously, with the third stage carried out in a batch process, as may be convenient.

Advantages of carrying out the first and optionally subsequent stages continuously include the possibility of the utilization of smaller, thus less expensive, reactors, as well as the other advantages mentioned above.

The invention is further illustrated by the following examples:

EXAMPLE 1

This example illustrates conduct of a two-step continuous process to produce the aromatic azomethine intermediate of 2-methyl-6-ethyl-N-ethoxymethyl-2-chloroacetanilide using a downflow flooded tubular evaporator.

The reactor/evaporator consisted of a 33 inch long 304 Stainless Steel column with a 7/16 inch inside diameter packed with 5 mm glass beads and equipped with an overhead condenser and a seal leg to control and maintain a constant level of liquid in the tube. The temperature in the top section of the tube was maintained at 75° to 90° C. and the bottom section of the tube 80° to 100° C.

A supply of formaldehyde-ethanol complex was prepared by mixing 20 moles (920 g) ethanol and 0.6 moles (61 g) triethylamine, followed by introducing 20 moles (659 g) paraformaldehyde prills (91%) and heating the resulting slurry to reflux at 89°–90° C. until a clear solution is formed.

The feed to the azomethine reactor had the following composition:

| Materials | Moles | Weight |
|---|---|---|
| 2-methyl-6-ethyl aniline | 1.0 | 138 gms |
| Xylene | 8.0 | 848 |
| Formaldehyde-ethanol complex (79.1 g/mole $CH_2O$ conc.) | 1.6 | 128 |

Feed was pumped continuously for 119 hours (interrupted) at rates ranging from 0.78 to 3.25 g/min to result in retention times ranging from 12 to 47 min. The reaction in the evaporator was conducted under 100 to 300 mmHg vacuum absolute to evaporate water by countercurrent contact with vapors to drive the azomethine reaction to completion.

The azomethine products were collected at various temperature and pressure conditions. The samples were then converted to 2-methyl-6-ethyl-N-ethoxymethyl-2-chloroacetanilide product by a derivatization procedure, first with chloroacetyl chloride at ambient conditions to form N-chloromethyl-α-chloroacetanilide. The chloroacetanilide was then reacted with 12 mole equivalents of anhydrous ethanol for 15 minutes; then gaseous ammonia was added to bring the pH to 8–9 to complete the conversion to the 2-methyl-6-ethyl-N-ethoxymethyl-2-chloroacetanilide product. The crude mixtures were analyzed by gas chromatography. The azomethine produced high quality product and relatively high conversions of the 2-methyl-6-ethyl-N-ethoxymethyl-2-chloroacetanilide with assays ranging from 95 to 97% as shown by the results summarized in Table 1.

| RUN # | RUN TIME [Hrs] | COLUMN TEMP [°C.] | MEA:$CH_2O$ [Ratio] | $R_t$ [Mins] | MEA [%] | PURITY GC A% Haloace- tanilide |
|---|---|---|---|---|---|---|
| 1 | 4 | 93 | (1:1.6) | 12 | 3 | 96 |
| 2 | 7 | 85 | (1:1.8) | 13 | 5 | 96 |
| 3 | 9 | 83 | (1:1.8) | 13 | 5 | 98 |
| 4 | 14 | 86 | (1:1.8) | 13 | 1 | 96 |
| 5 | 24 | 87 | (1:1.6) | 16 | 5 | 95 |
| 6 | 28 | 95 | (1:1.7) | 14 | 2 | 97 |
| 7 | 30 | 95 | (1:1.7) | 15 | 5 | 96 |
| 8 | 33 | 95 | (1:1.7) | 16 | 4 | 97 |
| 9 | 46 | 96 | (1:1.7) | 16 | 2 | 95 |
| 10 | 68 | 95 | (1:1.8) | 15 | 4 | 97 |
| 11 | 70 | 92 | (1:1.8) | 13 | 4 | 96 |
| 12 | 89 | 75 | (1:1.8) | 47 | 8 | 95 |
| 13 | 97 | 95 | (1:1.8) | 12 | 9 | 96 |
| 14 | 119 | 95 | (1:1.8) | 12 | 11 | 96 |

(MEA = 2-methyl-6-ethylaniline)

EXAMPLE 2

A 300 gallon reactor was charged with 300 lbs. of 95% paraformaldehyde (9.5 lb. moles) 437 lbs. of ethanol (9.5 lb. moles), and 19 lbs. (0.19 lb. moles) of triethylamine for production of the formaldehyde-ethanol complex. The mixture was heated to 66° C. and then charged with 882 lbs. of 98%, 2,6-methylethylaniline (6.4 lb. moles). The mixture was heated to reflux for 2 hours at 88° C. and subsequently distilled under atmospheric pressure to remove a portion of the water formed. The distillation was stopped when the reactor temperature reached 95° C.

The mixture was cooled and fed through a 50 gallon agitated tank and preheater into a falling film evaporator which consisted of a jacketed stainless steel pipe 3" i.d. and 16' long. The vapors (mainly water, ethanol and formaldehyde derivatives) were condensed overhead and collected in the receiver. The liquid from the bottom of the evaporator was collected as the azomethine product.

The evaporator was operated for 6.5 hours under 22–23 mmHg vacuum with the bottom temperature ranging from 125°–128° C. The feed flow to the evaporator varied between 0.28 and 0.52 gpm.

For evaluation purpose, samples taken from the azomethine product were converted to 2-methyl-6-ethyl-N-ethoxymethyl-2-chloroacetanilide by reacting the azomethine with chloroacetyl chloride to make N-chloromethyl-2-chloroacetanilide and then reacting that compound with ethanol according to the procedure described in U.S. Pat. No. 5,399,759. The purity of the ethoxymethyl acetanilide product was found to be in the 95–98% range.

EXAMPLE 3

This example was carried out under the same conditions as Example 2 except that the feed mixture in the reactor was distilled to 110° C. under atmospheric pressure to remove the bulk of the reaction water.

In this case, the evaporator was operated for about 28 hours with feed flow in the 0.15–0.25 gpm range, a vacuum range of 20–28 mmHg, and a bottom temperature range of 107°–124° C.

Samples of the azomethine product from the bottom of the falling film evaporator were converted to 2-methyl-6-ethyl-N-ethoxymethyl-2-chloroacetanilide as in Example 2, obtaining purities as high as 98.6% and non-chloromethylated haloacetanilide impurity concentration as low as 0.5%.

EXAMPLE 4

This example illustrates the conduct of the second step of the process in a continuous stirred tank reactor (CSTR). A 50 ml glass reactor equipped with a magnetic mixer, overhead condenser, a thermowatch and a heating bath was continuously charged with 10.2 g/min. of a 24% solution of the azomethine in xylene and 2.4 g/min. of chloroacetyl chloride. The reactor was kept at 114° C. The flow of N-chloromethyl-2-chloroacetanilide out of the reactor was regulated to maintain a residence time of 1.8 minutes. For evaluation purpose, the N-chloromethyl-2-chloroacetanilide product leaving the reactor was quenched in a large amount of ethanol to convert it to 2-methyl-6-ethyl-N-ethoxymethyl-2-chloroacetanilide. The product was analyzed to have a purity of 96.8 wt. %. The concentration of non-chloromethylated haloacetanilide was 0.7 wt. %. The yield (with respect to methylethylaniline used in the manufacture of the azomethine) was 92.7%.

EXAMPLE 5

This example illustrates conducting the third step in a CSTR. A 500 ml glass CSTR, equipped with a heating mantle and temperature control was charged continuously with 3.0 g/min of a 33% solution of N-chloromethyl-2-chloroacetanilide in xylene (prepared using the procedure described in Example IV B of U.S. Pat. No. 5,399,759. The volume of the reaction mixture was adjusted to achieve a constant residence time of 34 minutes. The outflow from the reactor was continuously charged into a neutralizer consisting of 150 ml glass CSTR equipped with a magnetic agitator and pH control system. Tributylamine charge to the neutralizer was adjusted by the pH control system to maintain the pH in the neutralizer at 7.5–8.5 range. The 2-methyl-6-ethyl-N-ethoxymethyl-2-chloroacetanilide product from the neutralizer was collected in a receiver from which it was sampled, washed and stripped in a rotary evaporator. The purity of the product was 97.2 wt % with 2.8 wt % non-chloromethylated haloacetanilide impurity.

What is claimed is:

1. In a process for the production of an aromatic azomethine by reaction of an aniline with formaldehyde in which the formaldehyde is provided in the form of a product produced by contacting paraformaldehyde with from about 0.25 to about 3 mole equivalents of an aliphatic alcohol having from one to four carbon atoms in the presence of a catalytic amount of a base, the steps comprising (a) conducting the reaction continuously and (b) continuously evaporating water of reaction from the reaction mixture, wherein steps (a) and (b) are conducted by passing the reaction mixture through one or more evaporators.

2. A process according to claim 1 in which the evaporators are countercurrent contact evaporators.

3. A process according to claim 1 in which step (a) is conducted in a continuous stirred tank reactor.

4. A process according to claim 1 in which steps (a) and/or (b) are conducted in two or more continuous upflow evaporators.

5. A process according to claim 1 in which steps (a) and/or (b) are conducted in one or more falling film evaporators, downflow flooded evaporators, or combination evaporators having an upper falling film section and a lower flooded section.

6. A process according to claim 1 in which steps (a) and/or (b) are conducted in one or more evaporators in which an inert gas or condensible gas is sparged into the lower section of the evaporator.

7. A process according to claim 1 in which the azomethine production is carried out in the presence of an inert solvent.

8. A process according to claim 1 in which the azomethine production is carried out in the absence of an inert solvent.

9. A process according to claim 1 further comprising continuously reacting the azomethine product of step (b) with a haloacetylating agent to produce an alpha-halo-N-halomethylacetanilide.

10. A process according to claim 9 further comprising continuously reacting the alpha-halo-N-halomethylacetanilide with an aliphatic alcohol to produce an N-alkoxyalkyl-alpha-haloacetanilide.

* * * * *